(12) United States Patent
Clodius-Talmadge

(10) Patent No.: US 7,913,694 B2
(45) Date of Patent: Mar. 29, 2011

(54) PROTECTIVE SHIELD AND COVER

(76) Inventor: Julie Clodius-Talmadge, Palmyra, VA (US)

( * ) Notice: Subject to any disclaimer, the term of this patent is extended or adjusted under 35 U.S.C. 154(b) by 0 days.

(21) Appl. No.: 11/851,978

(22) Filed: Sep. 7, 2007

(65) Prior Publication Data
US 2009/0065008 A1 Mar. 12, 2009

(51) Int. Cl.
A61F 6/06 (2006.01)
A61F 6/14 (2006.01)
A61F 5/37 (2006.01)
A61C 5/14 (2006.01)

(52) U.S. Cl. ......... 128/830; 128/841; 128/846; 128/859

(58) Field of Classification Search .................. 128/830, 128/831, 841, 846, 859, 898, 849; 604/385.05
See application file for complete search history.

(56) References Cited

U.S. PATENT DOCUMENTS

| | | |
|---|---|---|
| D31,271 S | 7/1899 | Halleck |
| 1,517,166 A | 11/1924 | Powers |
| 1,907,063 A | 5/1933 | Golanke |
| 3,176,686 A | 4/1965 | Barnes |
| 3,339,208 A | 9/1967 | Marbach |
| 3,782,375 A | 1/1974 | Donars |
| 4,449,980 A * | 5/1984 | Millar et al. ............ 424/430 |
| 4,807,600 A * | 2/1989 | Hayes ...................... 600/203 |
| 4,942,891 A | 7/1990 | Trevisan |
| 4,977,672 A | 12/1990 | Hamilton |
| 4,982,450 A | 1/1991 | D'Huissier |
| 5,174,307 A | 12/1992 | Thompson |
| 5,207,233 A | 5/1993 | Barnes |
| 5,450,671 A | 9/1995 | Harshman |
| D364,262 S | 11/1995 | Magidson et al. |
| 5,467,482 A | 11/1995 | Crawford, II |
| 5,483,705 A | 1/1996 | DiMatteo |
| 5,669,395 A | 9/1997 | Thompson |
| D395,735 S | 7/1998 | Paramore |
| 5,827,302 A | 10/1998 | Kandarian et al. |
| 5,832,535 A | 11/1998 | Davis |
| 5,842,474 A | 12/1998 | Blyskal et al. |
| 5,884,340 A | 3/1999 | Chen et al. |
| 5,885,204 A * | 3/1999 | Vergano .................. 600/29 |
| 6,319,219 B1 | 11/2001 | Landi |
| 6,336,462 B1 | 1/2002 | Santelli et al. |
| 6,655,389 B2 | 12/2003 | Bertucci |
| 6,681,771 B2 * | 1/2004 | Durette .................. 128/859 |
| 7,051,379 B2 | 5/2006 | Lambert |
| 7,296,307 B2 * | 11/2007 | Atwater et al. .......... 2/466 |
| 2004/0158221 A1 | 8/2004 | Mizutani et al. |
| 2005/0000536 A1 | 1/2005 | Notorio |
| 2005/0205105 A1 | 9/2005 | Demko |
| 2006/0254608 A1 | 11/2006 | Lam |
| 2007/0244352 A1 * | 10/2007 | Ziv .................... 600/29 |

FOREIGN PATENT DOCUMENTS
WO  WO2005/002387  5/2005

* cited by examiner

Primary Examiner — Patricia M Bianco
Assistant Examiner — Ophelia Hawthorne

(57) ABSTRACT

Protective shield and protective or ornamental cover for protecting the vulva and labia minora of a female. The protective shield is shaped to conform to the outer shape of the labia minora and protects the vulva of a female user.

20 Claims, 4 Drawing Sheets

PROTECTIVE SHIELD AND COVER

BACKGROUND OF INVENTION

The present invention pertains generally to hair removal products, and more particularly to a protective shield and cover for protecting the vulva and labia minora of a female.

As the demand for bikini hair removal procedures increase, so does the demand for related products. There are many methods for removing unwanted pubic hair, including waxing, shaving, using a depilatory, and laser hair removal. Waxing, such as the "brazilian wax", is a particularly popular choice, and is offered at many beauty salons and spas. Laser removal is becoming increasingly popular due to its success with permanently removing unwanted hair. Hair removal in a female's pubic region typically requires full exposure of the vulva area to ensure complete hair removal, placing the sensitive regions of the female genitalia at risk for damage and pain.

SUMMARY OF INVENTION

Embodiments of the invention include a protective shield comprising a main body shaped and adapted to be positioned so as to cover the labia minora and vulva of the female, the main body having a cap and two opposing lateral sides extending from the cap and joined together at opposing ends of the cap to form a cavity, the main body positionable over the labia minora of the female with the lateral sides fitting between the labia minor and labia major of the female such that the vulva and labia minora are covered by the main body and held in place only by the natural contours of the labia minora.

Embodiments of the invention may also include an outer cover for placement over the main body of the protective shield, wherein the outer cover includes an inner cavity that substantially conforms to an outer surface of the main body. The outer cover may be used for both protective purposes and ornamentation.

BRIEF DESCRIPTION OF THE DRAWINGS

A more complete appreciation of this invention, and many of the attendant advantages thereof, will be readily apparent as the same becomes better understood by reference to the following detailed description when considered in conjunction with the accompanying drawings in which like reference symbols indicate the same or similar components, wherein.

DETAILED DESCRIPTION

Figure 1:
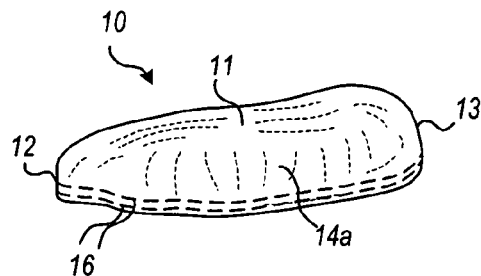
FIG. 1 is a perspective view of an exemplary embodiment of a protective shield.
Figure 2:
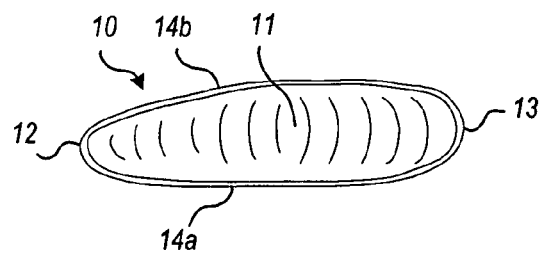
FIG. 2 is a top view of the protective shield of FIG. 1.
Figure 3:
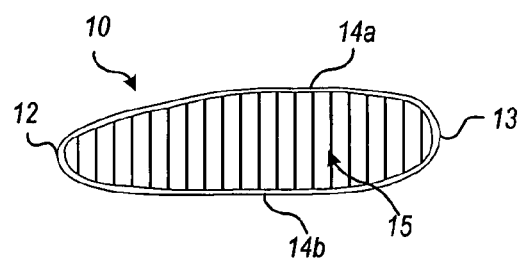
FIG. 3 is a bottom view of the protective shield of FIG. 1.
Figure 4:
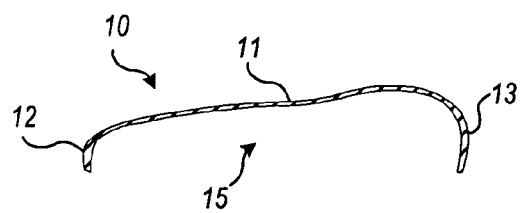
FIG. 4 is a lengthwise cross-sectional view of the protective shield of FIG. 1.
Figure 5:
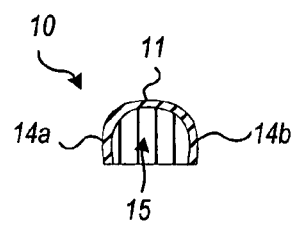
FIG. 5 is a crosswise cross-sectional view of the protective shield of FIG. 1.
Figure 6:
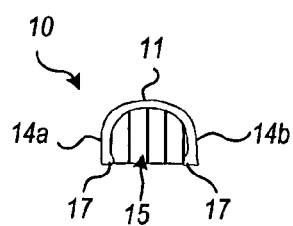
FIG. 6 is a perspective view of an exemplary embodiment of an outer cover for the protective shield of FIG. 1.
Figure 7:
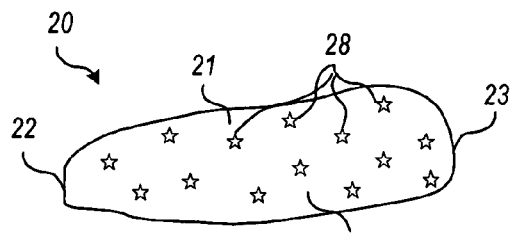
FIG. 7 is a top view of the outer cover of FIG. 6.
Figure 8:
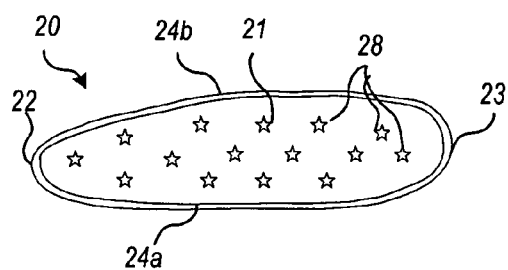
FIG. 8 is a bottom view of the outer cover of FIG. 6.
Figure 9:
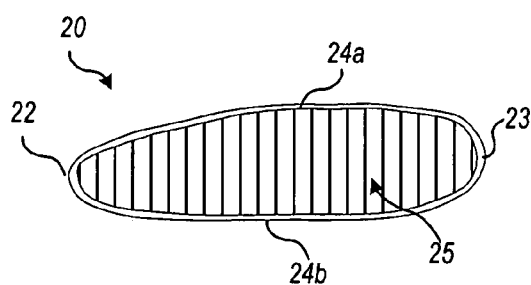
FIG. 9 is a crosswise cross-sectional view of the outer cover of FIG. 6.
Figure 10:
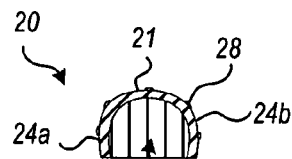
FIG. 10 is a lengthwise cross-sectional view of the outer cover of FIG. 6.
Figure 11:
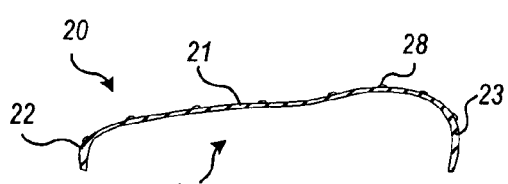
FIG. 11 is a perspective view illustrating the installation of the outer cover of FIG. 6 over the protective shield of FIG. 1.
Figure 12:
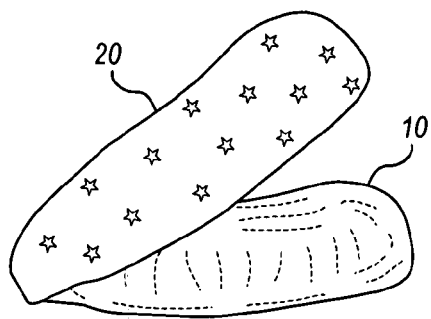
FIG. 12 is a perspective view of the outer cover of FIG. 6 installed over the protective shield of FIG. 1.
Figure 13:
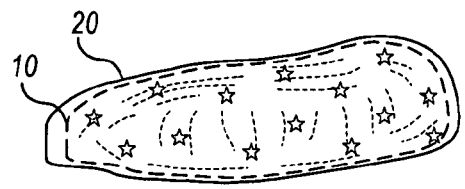
FIG. 13 is a lengthwise cross-sectional view of the outer cover of FIG. 6 installed over the protective shield of FIG. 1.
Figure 14:
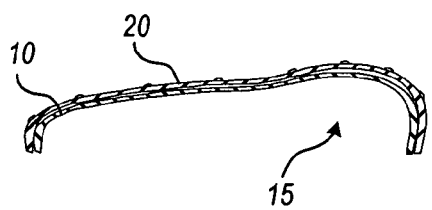
FIG. 14 is a crosswise cross-sectional view of the outer cover of FIG. 6 installed over the protective shield of FIG. 1.

Embodiments of the invention provide a protective shield for removal of hair in the female genital area. Such techniques may include, but are not limited to, waxing, laser removal, electrolysis removal, shaving, and use of depilatory creams, gels or sprays.

Referring now to the embodiment of FIGS. 1-20, there is shown a protective shield 10 for use in protecting the female genital area, i.e., the vulva 36 and the delicate membrane of the vaginal and urethral openings, the labia minora 34 and all other very sensitive features. The protective shield 10 is generally shaped to fit over the entire labia minora 34 of a human female, and is designed to fit between the labia minora 34 and the labia majora 32 with the protective shield 10 positioned around and over, and held in place by, the labia minora 34.

As best shown in FIGS. 1-5, the protective shield 10 is generally formed of a main body integrally comprising a cap 11 and two opposing lateral sides 14a, 14b extending from the cap 11 and joined together at opposing ends 12, 13 of the cap 11 to form a cavity 15 which substantially conforms to the shape of the labia minora 34.

Figure 18:
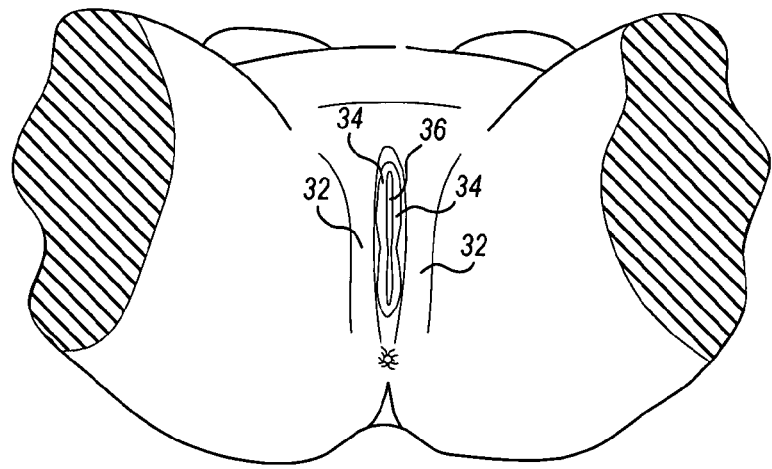
FIG. 18 is a view of the perineum of the human female.
Figure 19:
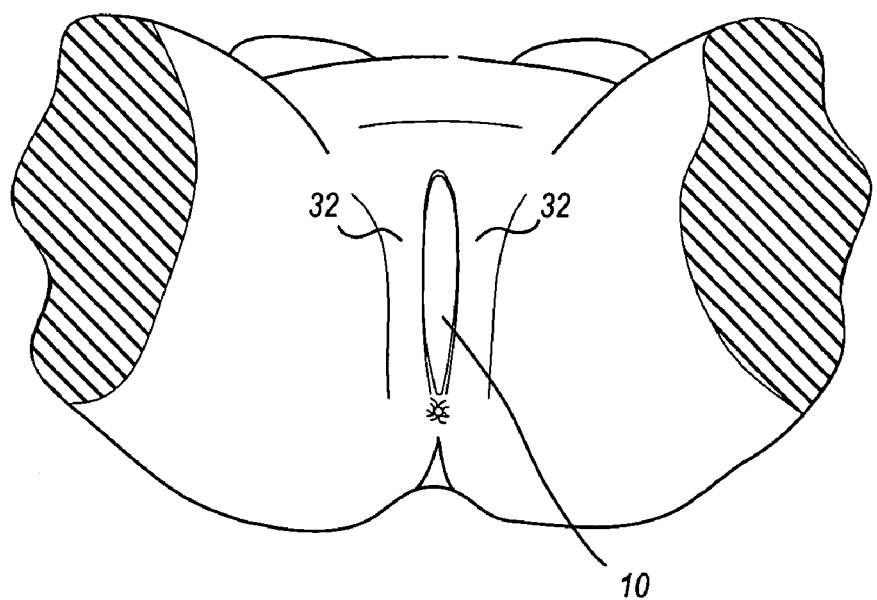
FIG. 19 is a view of the perineum of the human female with a protective shield installed.
Figure 20:
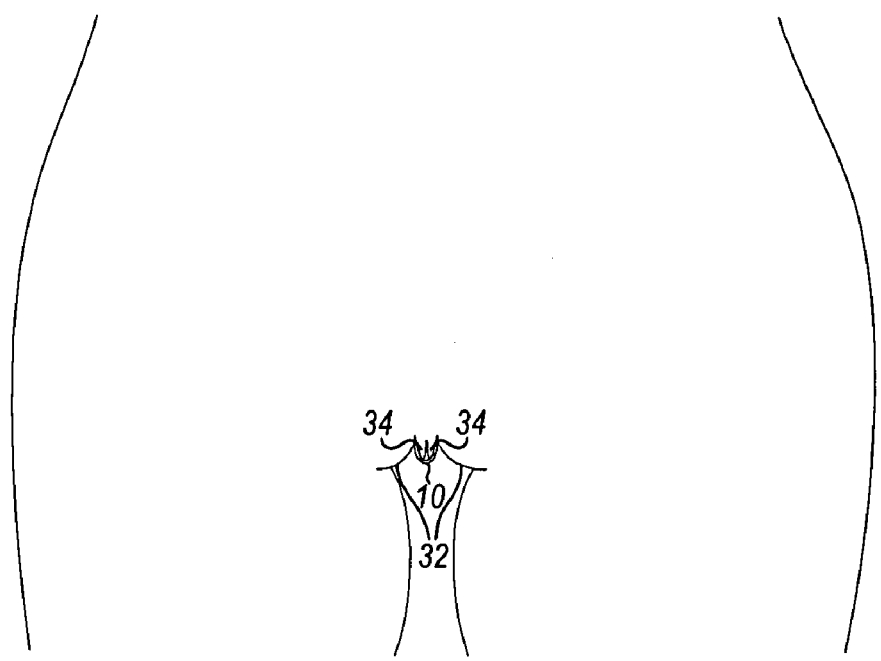
FIG. 20 is a front cross-sectional view of the perineum of the human female with the protective shield of the embodiment of FIG. 1 installed.

During use, as illustrated in FIGS. 18-20, the protective shield 10 is positioned over the labia minora 34 of the female with the lateral sides 14a, 14b, fitting between the labia minora 34 and labia majora 32 of the female such that the vulva 36 and labia minora 34 are covered by the cap 11, and such that the labia minora 34 fits within the cavity 15 of the protective shield 10. The protective shield 10 is self-held in place by the natural contours of the labia minora 34. In an embodiment, illustrated in FIG. 6, the outer edges of the lateral sides are configured with a ridge formation 17 which provide additional gripping action.

In an embodiment, the protective shield 10 is formed of a soft rubbery polymer material, which naturally grips the labia minora 34 of the user, and due to its non-breathable characteristics, may be installed over the labia minora 34 so as to form a vacuum, which further assists in holding the protective shield 10 in place when positioned in place over the labia minora 34 via suction action. The soft rubbery polymer material may be, by way of illustration only and not limitation, an elastomer or ethylene-vinyl acetate (EVA). The material may also be silicon, which disperses and reflects light energy so as to prevent penetration of light energy completely through the material when used for laser hair removal. The material may also be made of other materials, such as rubber, plastic, vinyl, etc. In an embodiment, the color of the protective shield 10 is a color that substantially disperses and reflects, or blocks, light energy so as to prevent penetration of the light energy through the shield.

The cavity 15 of the protective shield 10 is formed to accommodate labia minora 34 of different sizes and shapes that may exist because of the difference between the anatomies of females, especially on the upper aspect of the genital area, where some patients have a larger clitoris or labia minora 34. As stated above, the protective shields 10 of the embodiments of the invention are made of a soft rubbery polymer to provide for a better and more comfortable fit regardless of the individual features of the patient. With this shape and construction, the protective shield 10 will fit most patients so that the user's entire labia minora 34 is covered. To accommodate different sizes of labia minora 34, the protective shield 10 may be made in different sizes. Alternatively, the main body of the protective shield 10 may be formed with indicator lines along the edges of the lateral sides of the main body to guide a user or practitioner in decreasing the depth of the cavity of the protective shield 10. In other words, the user or practitioner may use the indicator lines 16 to cut the protective shield 10 down to size to fit the user. The size selected size is specific to the user.

Figure 15:
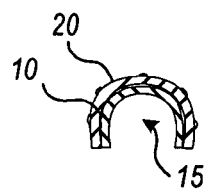
FIG. 15 is a view of the perineum of the human female.
Figure 16:
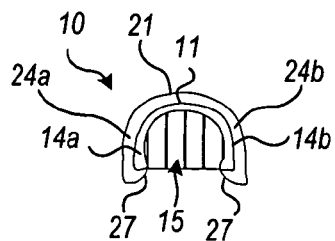
FIG. 16 is a view of the perineum of the human female with a protective shield installed.
Figure 17:
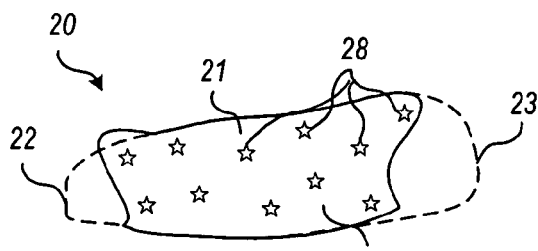
FIG. 17 is a front cross-sectional view of the perineum of the human female with the protective shield installed.

In an embodiment, illustrated in FIGS. 12-17, the protective shield 10 includes an outer cover 20 which may be used to prevent penetration of light energy to the shield, and/or for ornamentation. In one embodiment, the outer cover 20 is removable from the protective shield 10. In another embodiment, the outer cover 20 is non-removable from the protective shield 10. The outer surface of the outer cover 20 may be of any shape, for example conforming to the shape of the protective shield as shown in FIGS. 12-15, or of any other shape, for example as shown in FIG. 17. However, the inner surface of the outer cover 20 forms a cavity 25 which substantially conforms to an outer surface of at least a portion of the main body of the protective shield 10 over which the outer cover 20 is configured to be positioned. The protective shield 10 may include means for retaining the protective shield 10 within the cavity when placed over the protective shield 10. In an embodiment, the retaining means is the implementation of the protective shield 10 with a soft polymer material that naturally grips the inner surface of the protective shield 10 through friction, as illustrated in FIG. 15. Other retaining means, such as an inward-formed ridge 27 as shown in FIG. 16. Other retaining means may include mating grooves or ridges, clips, snaps, etc.

In an embodiment, the outer cover 20 is made of a material which blocks, disperses, and/or reflects light energy.

In one embodiment, the outer cover 20 is made of a metal such as, but not limited to, silver, platinum, or gold.

In one embodiment, the outer cover 20 includes ornamentation such as, but not limited to, embedded jewels 28 or precious stones, engravings, and enamels.

The installation of the protective shield 10 (with or without the outer cover 20) can be performed by the user herself or a hair removal practitioner. The presence of the protective shield 10 between the labia minora 34 and the labia majora 32 enables the practitioner to stretch the labia majora 32 in order to expose the hair that is to be removed by lasing the hair follicles.

As described above, the protective shield 10 is specifically contoured to fit over the woman's labia minora 34 and held in place by custom fit inside the labia majora 32. When installed over the labia minora 34 to remove as much air as possible, the protective shield 10 may also stay in place due to suction action. This design allows the user or practitioner to stretch the labia majora 32 in order to expose all hair for removal.

In an embodiment, the thickness the outer cover 20 is approximately 0.5 mm-1 mm, depending on the material used to form the outer cover 20. The soft inner protective shield 10 is generally 2 mm-3 mm thick. In an embodiment, the shield 10 is approximately 1.5 cm in width, 7.5 cm in length, and 1.5 cm-2 cm in height before trimmed to custom fit. Although one size may be made to accommodate most women, it may be desirable to make each protective shield 10 in more than one size or to provide one size with indicator lines 16 that allow an individual user to trim the size specific to the user.

The unique fitted design of the protective shield 10 with or without the outer cover 20 is suited for placement by the user for home use or to wear to a hair removal practitioner's office or salon for personal cover. Although described herein with respect to use in hair removal procedures, the protective shield 10 with or without the outer cover 20 is also ideal for use in nude sunbathing and in surgical procedures performed near the sensitive vulva area.

Although this preferred embodiment of the present invention has been disclosed for illustrative purposes, those skilled in the art will appreciate that various modifications, additions and substitutions are possible, without departing from the scope and spirit of the invention as disclosed in the accompanying claims.

What is claimed is:

1. A protective shield, said protective shield comprising:
   a cap,
   two opposing lateral sides extending from the cap and joined together at opposing ends of the cap to form a cavity which substantially conforms to the shape of the labia minora of a female, and
   one or more ridge formations disposed on an inner surface of the cavity and configured to provide retention force against the labia minora when the protective shield is installed over the labia minora of the female with the two opposing lateral sides fitting between the labia minora and labia majora of the female such that the two opposing lateral sides naturally grip the labia minora.

2. The protective shield of claim 1, comprising an outer cover having an inner cavity that substantially conforms to an outer surface of at least a portion of the protective shield over which the outer cover is configured to be positioned.

3. The protective shield of claim 2, wherein the outer cover comprises a metal material.

4. The protective shield of claim 2, wherein the outer cover comprises ornamentation.

5. The protective shield of claim 2, wherein the outer cover comprises retaining means for retaining the protective shield.

6. The protective shield of claim 2, wherein the outer cover is removable from the protective shield.

7. The protective shield of claim 2, wherein the outer cover is permanently attached to the protective shield.

8. The protective shield of claim 1 formed of a soft polymer material.

9. The protective shield of claim 1 formed of an ethylene vinyl acetate material.

10. The protective shield of claim 1, the lateral sides positioned to contact the outer surfaces of the labia minora so as to naturally grip the labia minora to thereby hold the protective shield in place.

11. The protective shield of claim 1, comprising a cupped end extending from the cap and joining the two lateral sides.

12. The protective shield of claim 1 made of a color that disperses, reflects, or blocks light energy so as to prevent penetration of the light energy completely through the material.

13. The protective shield of claim 1 further comprising indicator lines along the edges of the lateral sides for use as guides in decreasing the depth of the cavity of the protective shield.

14. An outer cover for a protective shield, the outer cover comprising:

a main body configured with an inner cavity that substantially conforms to an outer surface of at least a portion of the protective shield over which the outer cover is configured to be positioned, the protective shield comprising a cap, two opposing lateral sides extending from the cap and joined together at opposing ends of the cap to form a cavity which substantially conforms to the shape of the labia minora of a female, and one or more ridge formations disposed on an inner surface of the cavity and configured to provide retention force against the labia minora when the protective shield is installed over the labia minora of the female with the two opposing lateral sides fitting between the labia minora and labia majora of the female such that the two opposing lateral sides naturally grip the labia minora.

15. The outer cover of claim 14 formed of a metal material.

16. The outer cover of claim 14, wherein the outer cover comprises non-functional ornamentation.

17. The outer cover of claim 14, wherein the outer cover is removable from the protective shield.

18. The outer cover of claim 14, wherein the outer cover is permanently attached to the protective shield.

19. A method for protecting a vulva and labia minora of a human female, the method comprising:

installing a protective shield over the labia minora of the female, the protective shield comprising a cap, two opposing lateral sides extending from the cap and joined together at opposing ends of the cap to form a cavity which substantially conforms to the shape of the labia minora of a female, and one or more ridge formations disposed on an inner surface of the cavity and configured to provide retention force against the labia minora when the protective shield is installed over the labia minora of the female with the two opposing lateral sides fitting between the labia minora and labia majora of the female such that the two opposing lateral sides naturally grip the labia minora.

20. The method of claim 19, comprising:

installing an outer cover over the protective shield before or after installing the protective shield over the labia minora of the female.

\* \* \* \* \*